United States Patent [19]

Tokunaga et al.

[11] Patent Number: 5,152,999
[45] Date of Patent: Oct. 6, 1992

[54] LIPOSOME PREPARATION

[75] Inventors: Yuji Tokunaga, Sanda; Takao Yamamoto, Osaka; Takehisa Hata, Nagaokakyo, all of Japan

[73] Assignee: Fujisawa Pharmaceutical Co., Ltd., Osaka, Japan

[21] Appl. No.: 680,923

[22] Filed: Apr. 5, 1991

[30] Foreign Application Priority Data

Apr. 24, 1990 [JP] Japan .................. 2-109324

[51] Int. Cl.$^5$ .............................. A61K 9/127
[52] U.S. Cl. .................... 424/450; 552/544; 562/563; 562/576
[58] Field of Search ............ 424/450; 428/402.2; 264/4.1, 4.3, 4.6; 552/544; 562/563, 576

[56] References Cited

U.S. PATENT DOCUMENTS

| | | | |
|---|---|---|---|
| 4,721,612 | 1/1988 | Janoff et al. | 424/450 X |
| 4,804,539 | 2/1989 | Guo et al. | 424/450 |
| 4,927,571 | 5/1990 | Huang et al. | 264/4.3 |

OTHER PUBLICATIONS

Ahmad et al, "Lithium Aluminium Hydride-Aluminium Chloride Reduction of Steroidal Cyclic Acetals," Aust. J. Chem., 24: 143-151 (1971).

Primary Examiner—Thurman K. Page
Attorney, Agent, or Firm—Oblon, Spivak, McClelland, Maier & Neustadt

[57] ABSTRACT

The present invention relates to liposome preparations. In particular, the present invention relates to Adriamycin-entrapped liposome preparations comprising cholesterol derivatives having a negative charge as a liposome membrane constituent. Adriamycin-entrapped liposome preparations have many uses in the medical field such as maintaining high Adriamycin blood levels over a long period of time and reducing systemic toxicity, for example.

2 Claims, No Drawings

LIPOSOME PREPARATION

BACKGROUND OF THE INVENTION

1. Field of the Invention

The present invention relates to liposome preparations and more particularly, to liposome preparations comprising cholesterol derivatives having a negative charge as a liposome membrane constituent, in which Adriamycin is entrappped. The preparations are utilized in the medical field.

2. Statement of the Prior Art

Adriamycin has been widely used as an anti-tumor agent. Due to its positive charge in physiological pH region, however, Adriamycin encounters problems that Adriamycin binds to membrane constituents such as cells, mitochondria, etc., especially to phospholipids negatively charged, thus leading to accumulative cardiotoxicity as a cause therefor. Accordingly, its dosage is limited. In addition, Adriamycin has a high affinity to vital tissues so that even when it is intravenously administered, Adriamycin rapidly disappears out of blood.

In order to solve the foregoing problems, there are provided Adriamycin-entrapped liposome preparations in which acidic glycolipids such as Sulfatides having a negative charge in a physiological pH region, or glycolipids having a sulfo group, especially Sulfatides (Japanese Patent Application Laid-Open Nos. 62-129221 and 63-112512).

On the other hand, in Adriamycin-entrapped liposome preparations, it is known to use sterols having a negative charge such as cholesterol sulfate and cholesterol hemisuccinate as the liposome membrane constituent (International Patent Application No. PCT/US88/01573 : International Publication No. W088/09168).

The aforesaid liposome preparations obtained by incorporating Sulfatide into the liposome membrane constituent exhibit effects that they have a high content of Adriamycin to keep a high blood level of Adriamycin over a long period of time and less accumulate Adriamycin on the heart, as compared to the case where Adriamycin is administered in an aqueous solution and therefore, cardiotoxicity can be reduced.

However, it has not yet been established to chemically synthesize Sulfatides, but they are obtained by extracting and purifying from animal, e.g., bovine brain. For this reason, it is difficult to obtain pure compounds. In addition, extraction and purification take much time. In the case of utilizing commercially available compounds, costs are extremely high. Thus, there was a problem that liposome preparations containing these components as liposome membrane constituents could not be produced in large quantities from an industrial viewpoint.

As a result of extensive investigations on liposome membrane constituents which can be easily synthesized at low costs, the present inventors have found that cholesterol derivatives having a negative charge and represented by general formula:

R—CO—A₁

(wherein R represents a cholesterol residue, and A₁ represents an amino acid residue), and represented by general formula:

R—A₂

(wherein R represents a cholesterol residue, and A₂ represents a fatty acid residue), had effects equivalent to Sulfatide.

That is, it has been found that Adriamycin-entrapped liposome preparations comprising these cholesterol derivatives having a negative charge as liposome membrane constituents have a high content of Adriamycin and when administered in a living body, can maintain high blood level of Adriamycin over a long period of time, reduce distribution of Adriamycin on the heart and reduce systemic toxicity. The present invention has thus been completed.

DETAILED DESCRIPTION OF PREFERRED EMBODIMENTS

In the present specification, the cholesterol residue refers to a group obtained by removing hydrogen atom from the hydroxy group at the 3-position of cholesterol, and the amino acid residue refers to a group obtained by removing one hydrogen atom from the amino moiety of an amino acid. The fatty acid residue refers to a group obtained by removing one hydrogen atom from the hydrocarbon moiety of a fatty acid.

As the amino acid, an aliphatic amino acid is preferred. Among them, particularly preferred are a monoamino-monocarboxylic acid (for example, glycine, alanine, etc.) and a monoaminodicarboxylic acid (for example, aspartic acid, glutamic acid, etc.).

As the fatty acid, a lower fatty acid having 2 to 7 carbon atoms (for example, propionic acid, butyric acid, etc.) is preferred.

Examples of the cholesterol derivatives represented by general formula:

R—CO—A₁

(wherein R and A₁ have the same significances as described above) include:
N-(cholest-5-ene-3β-oxycarbonyl)glycine,
N-(cholest-5-ene-3β-oxycarbonyl)glycylglycine,
N-(cholest-5-ene-3β-oxycarbonyl)glycylglycylglycine,
N-(cholest-5-ene-3β-oxycarbonyl)-β-alanine,
N-(cholest-5-ene-3β-oxycarbonyl)-6-amino-n-caproic acid,
N (cholest-5-ene-3β-oxycarbonyl)-4-aminomethylbenzoic acid,
N-(cholest-5-ene-3β-oxycarbonyl)-4-aminophenylacetic acid,
N-(cholest-5-ene-3β-oxycarbonyl)-β-alanyl-β-alanine,
N-(cholest-5-ene-3β-oxycarbonyl)-β-alanyl-β-alanyl-β-alanine,
N-(cholest-5-ene-3β-oxycarbonyl)-β-alanyl-glycine,
N-(cholest-5-ene-3β-oxycarbonyl)phenylalanine,
N-(cholest 5-ene-3β-oxycarbonyl)aspartic acid, etc.

Examples of the cholesterol derivatives represented by general formula:

R—A₂

(wherein R and A₂ have the same significances as described above) include cholest-5-ene-3β-oxyacetic acid, cholest-5-ene-3β-oxypropionic acid, cholest-5-ene-3β-oxybutyric acid, etc.

Of these cholesterol derivatives, the cholesterol derivatives represented by general formula:

R—CO—A₁

(wherein R and A₁ have the same significances as described above) can be prepared, for example, by reacting reactive derivatives at the 3-hydroxy group of cholesterol with amino acid compounds.

As the reactive derivatives at the 3-hydroxy group of cholesterol, there are compounds in which the hydroxy group is converted into an acid residue, for example, a haloformyloxy (e.g., chloroformyloxy, etc.).

The reaction is generally carried out in a conventional solvent such as methanol, ethanol, acetone, dioxan, acetonitrile, chloroform, methylene chloride, ethylene chloride, tetrahydrofuran, ethyl acetate, N,N-dimethylformamide, pyridine, etc. The reaction may be carried out in any other solvent as far as the solvent is inert to the reaction. These conventional solvents may be used as admixture with water.

The reaction may also be carried out in the presence of an inorganic base or an organic base such as alkali metal hydrogencarbonate (e.g., sodium hydrogen-carbonate, etc.), tri(lower)alkylamine (e.g., trimethylamine, triethylamine, etc.), pyridine, N-(lower)alkylmorpholine, N,N-di(lower)alkylbenzylamine, etc. The reaction temperature is not particularly limited; in general, the reaction is carried out under cooling or at normal temperature.

Furthermore, the cholesterol derivatives represented by general formula:

R—A₂

(wherein R and A₂ have the same significances as described above) can be prepared in accordance with the process described in Aust. J. Chem., 24, 143-151 (1971).

As the phospholipid used as the liposome membrane constituent upon preparing the liposome preparation of the present invention, together with the cholesterol derivatives described above, there are phospholipids derived from yolk, soybean and other animal tissues such as phosphatidylcholine, phosphatidylethanolamine, phosphatidylinositol, phosphatidylserine, sphingomyelin, etc., soybean lecithin which is a mixture of the phospholipids described above; and synthetic lecithin such as dipalmitoyllecithin, distearoyllecithin, etc.

In preparing the liposome preparation of this invention, it is desired to add the cholesterol derivative and Adriamycin in equimolar amounts. A constitutional molar ratio of the cholesterol derivative to the phospholipid in the liposome membrane constituents is approximately 1:1000 to 1:1.

In addition to the cholesterol derivative and the phospholipid, the liposome preparation of the present invention may appropriately contain ordinary additives, for example, cholesterol, dicetyl phosphate, α-tocopherol, etc.

The liposome preparation of the present invention can be prepared by known methods. That is, Adriamycin and the cholesterol derivative and the liposome membrane constituents such as phospholipids, additives, etc. are dissolved in a suitable solvent such as chloroform, methanol, ethanol, etc. The solution is charged in an appropriate vessel and the solvent is distilled off under reduced pressure. Next, a surfactant (e.g., sodium cholate, etc.) and an aqueous solution (e.g., phosphate buffered physiological saline, etc.) are added to the residue followed by shaking. After solubilizing the residue, the surfactant is removed from the solution using a device for removing surfactant. The liposome preparation can thus be prepared.

Alternatively, the liposome preparation can also be prepared by dissolving the liposome membrane constituents described above in an organic solvent such as chloroform, ethanol, etc., charging the solution in an appropriate vessel, distilling off the solvent under reduced pressure to form a thin membrane onto the inner surface of the vessel, then charging an aqueous solution of Adriamycin in the vessel, and shaking or performing sonication.

Furthermore, the liposome preparation can also be prepared by dissolving the liposome membrane constituents described above and Adriamycin in an organic solvent such as chloroform, ethanol, methanol, etc., charging the solution in an appropriate vessel, distilling off the solvent under reduced pressure to form a thin membrane onto the inner surface of the vessel, then charging phosphate buffer in the vessel, and shaking or performing sonication.

Furthermore, the liposome preparation may also be prepared in a conventional method such a ether injection method, etc. The method for preparing the liposome preparation of the present invention is not particularly limited.

The thus prepared liposome preparation of the present invention is administered, for example, by parenteral administration (e.g., intravenous injection, intramuscular injection, injection into tumor, etc.), oral administration, rectal administration, etc.

Hereafter the effects of the present invention are explained with reference to test examples.

TEST EXAMPLE 1

Method

The liposome suspensions prior to and after dialysis obtained in Examples 1 through 5 and Reference Example 1 later described were diluted with ethanol, respectively. An amount of Adriamycin was determined by high performance liquid chromatography (UV 254 nm) and the content of Adriamycin included was calculated by the following equation.

Amount of Adriamycin entrapped (%) =

$$\frac{\text{total amount of Adriamycin contained in liposome suspension after dialysis}}{\text{total amount of Adriamycin contained in liposome suspension prior to dialysis}} \times 100$$

TABLE 1

| Liposome Preparation | Results Amount of Adriamycin Entrapped |
| --- | --- |
| Example 1 | 84.8% |
| Example 2 | 74.1% |
| Example 3 | 51.1% |
| Example 4 | 74.8% |
| Example 5 | 83.8% |
| Reference Example 1 | 20.0% |

In the liposome preparation of the present invention, the amount of Adriamycin entrapped is higher than the liposome preparation of Reference Example 1 (no cholesterol derivative was added).

TEST EXAMPLE 2

Method

A solution of Adriamycin in physiological saline (concentration: 2 mg/ml) and the liposome preparation obtained in Example 1 later described were administered to male ICR strain mice weighing 30 to 35 g from the tail vein, in doses of 20 mg/kg and 8 mg/kg, respectively, when calculated as Adriamycin. After a definite period of time, the heart was ectomized. The heart was washed with physiological saline and an amount of Adriamycin distributed was determined by a modification of the method described in Cancer Chemother. Rep., 54(2), 89-94 (1970).

TABLE 2

| | Results Distribution of Adriamycin in Heart (% of dose/tissue) | | | |
|---|---|---|---|---|
| | 5 min. | 15 min. | 30 min. | 4 hour. |
| Example 1 | 0.42 ± 0.02 | 0.30 ± 0.00 | 0.20 ± 0.01 | 0.18 ± 0.02 |
| Aqueous solution | 0.77 ± 0.13 | 0.65 ± 0.01 | 0.76 ± 0.10 | 0.36 ± 0.03 |

(n = 3, mean ± standard error)

When the liposome preparation of the present invention was administered, it is understood that distribution of Adriamycin in heart is prevented, as compared to the case of administering the aqueous solution.

TEST EXAMPLE 3

Method

A solution of Adriamycin in physiological saline (concentration; 2 mg/ml) and the liposome preparations obtained in Examples 1 through 4 later described were administered to SD strain male rats weighing 290 to 320 g from the femoral vein, in doses of 1 to 4 mg/kg, respectively, when calculated as Adriamycin. At each time point, blood was collected from the infraclavicular vein. Using 0.2 ml of whole blood, blood concentration of Adriamycin was determined by a modification of the method described in Cancer Chemother. Rep., 54(2), 89–94 (1970).

TABLE 3

| | Results Concentration of Adriamycin in Whole Blood (% of dose/ml) | | | | | | | |
|---|---|---|---|---|---|---|---|---|
| | 2.5 min | 5 min | 15 min | 30 min | 1 hr | 2 hr | 4 hr | 6 hr |
| Example 1 | 3.196 ± 0.333 | 2.844 ± 0.167 | 2.159 ± 0.218 | 1.495 ± 0.139 | 0.880 ± 0.097 | 0.259 ± 0.039 | 0.072 ± 0.010 | 0.035 ± 0.009 |
| Example 2 | 3.383 ± 0.217 | 2.659 ± 0.177 | 1.679 ± 0.150 | 1.231 ± 0.116 | 0.816 ± 0.089 | 0.433 ± 0.062 | 0.165 ± 0.036 | 0.065 ± 0.016 |
| Example 3 | 2.661 ± 0.011 | 1.658 ± 0.100 | 0.772 ± 0.126 | 0.483 ± 0.079 | 0.316 ± 0.065 | 0.142 ± 0.029 | 0.049 ± 0.010 | 0.040 ± 0.002 |
| Example 4 | 2.046 ± 0.116 | 1.378 (n = 2) | 0.851 ± 0.178 | 0.527 ± 0.119 | 0.333 ± 0.086 | 0.170 ± 0.046 | 0.061 ± 0.031 | 0.030 ± 0.015 |
| aqueous solution | 0.640 ± 0.032 | 0.161 ± 0.010 | 0.042 ± 0.001 | 0.026 ± 0.001 | 0.018 ± 0.001 | 0.019 ± 0.001 | 0.014 ± 0.000 | 0.013 ± 0.001 |

(n = 2 to 4, mean ± standard error)

When the liposome preparation of the present invention was administered, it is understood that high blood concentration of Adriamycin can be maintained, as compared to the case of administering the aqueous solution.

TEST EXAMPLE 4

Method

A solution of Adriamycin in physiological saline (concentration: 2 mg/ml) and the liposome preparation obtained in Example 1 later described were administered to ICR strain male mice weighing 30 to 35 g from the tail vein, all in a dose of 32 mg/kg, when calculated as Adriamycin. A survival rate and body weight change of mice on Day 14 were observed and the results were compared with those obtained with mice for control group to which no Adriamycin was administered.

TABLE 4

| | Results | |
|---|---|---|
| | Survival Rate (%) | Body Weight Change (%) |
| Example 1 | 89 | 96.2 |
| Aqueous solution | 30 | 85.2 |
| Control | 100 | 116.9 |

On Day 14 after the aqueous solution of Adriamycin, the survival rate of mice was reduced to 30% (3 out of 10 cases) and the body weight decreased to 85.2% prior to the administration; whereas on Day 14 after administration of the liposome preparation of this invention, the survival rate of mice was 89% (8 out of 9 cases) and the body weight showed 96.2%, indicating that the degree of decrease was small. It is noted from the results that systemic toxicity was alleviated.

REFERENCED EXAMPLE 1

After 10.9 ml of a solution of 37.5 μmoles of Adriamycin in methanol was charged in an Erlenmeyer's flask, the organic solvent was distilled off by an evaporator. Then 14.4 ml of a solution of 225.2 μmoles of yolk lecithin and 150 μmoles of cholesterol in chloroform was further charged in the flask. Chloroform was then distilled off by the evaporator.

After 10 ml of 0.01 M of phosphate buffered saline was added to the residue, the mixture was shaken to give a liposome suspension. The resulting liposome suspension was sequentially extruded through polycarbonate membranes (3.0, 1.0, 0.8, 0.6 and 0.4 μm). Thereafter, Adriamycin which was not entrapped in liposome was removed by dialysis in 0.001 M phosphate buffered saline at 4° C. for 48 to 72 hours. Thus, Adriamycin-entrapped liposome preparation was obtained.

Hereafter the present invention is described in more detail with reference to preparation examples and examples.

PREPARATION EXAMPLE 1

To a suspension of glycine (1.50 g) in water (100 ml) was added triethylamine (4.04 g). After dioxan (200 ml) and cholesteryl chloroformate (8.98 g) were added to the resulting clear solution at 0° C., the mixture was stirred for 3 hours. The reaction mixture was concentrated under reduced pressure and, 1 N hydrochloric acid (23 ml) and chloroform (100 ml) were added to the residue. The organic phase was separated and washed with water and then dried over magnesium sulfate. The solvent was distilled off to give crude crystals. After washing with ethanol, the crystals were filtered to give N-(cholest-5-ene-3β-oxycarbonyl)glycine (6.64 g) as white crystals.

Melting point: 175–177° C. (decomposed)
IR (nujol): 3320, 1750, 1665, 1570 cm$^{-1}$

PREPARATION EXAMPLE 2

Sodium hydrogencarbonate (0.168 g) and tetrahydrofuran (20 ml) were added to a suspension of glycylglycine (0.15 g) in water (20 ml). After tetrahydrofuran (20 ml) and cholesteryl chloroformate (0.898 g) were added to the resulting transparent solution at 0° C., the mixture was stirred for an hour. The reaction mixture was concentrated under reduced pressure and, methanl (10 ml) and chloroform (10 ml) were added to the residue. By filtration, the transparent solution was obtained. The solvent was distilled off to give crude crystals (0.98 g). The crude crystals were then purified by silica gel chromatography to give N-(cholest-5-ene-3β-oxycarbonyl)-glycylglycine (0.5 g) as white powders.

Melting point: 223–225° C (decomposed)

PREPARATION EXAMPLE 3

N-(Cholest-5-ene-3β-oxycarbonyl)glycylglycylglycine (0.41 g) was obtained as white powders in a manner similar to Preparation Example 2, except for using glycylglycylglycine (0.22 g) instead of glycylglycine (0.15 g).

Melting point: 235–239° C. (decomposed)

PREPARATION EXAMPLE 4

Sodium hydrogencarbonate (168 mg) was added to a solution of p-aminomethylbenzoic acid (303 mg) in a mixture of tetrahydrofuran (5 ml) and water (20 ml). Tetrahydrofuran (20 ml) and cholesteryl chloroforamate (898 mg) were added to the solution at 0° C. The mixture was stirred for 3 hours. The reaction mixture was concentrated under reduced pressure and, 1 N hydrochloric acid (30 ml) and chloroform (30 ml) were added to the residue. The organic phase was separated and washed with water and then dried over magnesium sulfate. The solvent was distilled off to give crude crystals. After washing with ethanol, the crystals were filtered to give N-(cholest-5-ene-3β-oxycarbonyl)-4-aminomethylbenzoic acid (500 mg) as white solids.

Melting point: 175–177° C. (decomposed)

PREPARATION EXAMPLE 5

The following compound was obtained in a manner similar to Preparation Example 4, except for using p-aminophenylacetic acid instead of p-aminomethylbenzoic acid. N-(cholest 5-ene-3β-oxycarbonyl)-4-aminophenylacetic acid (907 mg)

Melting point: 170–172° C. (decomposed)

PREPARATION EXAMPLE 6

Tetrahydrofuran (20 ml) and cholesteryl chloroformate (449 mg) were added to a solution of β-alanine (56 mg) and sodium hydrogencarbonate (84 mg) in water (10 ml) at 0° C. The mixture was stirred for an hour. The reaction mixture was concentrated under reduced pressure and, 0.1 N hydrochloric acid (10 ml) and chloroform (40 ml) were added to the residue. The organic phase was separated and washed with water and then dried over magnesium sulfate. The solvent was distilled off to give crude crystals. The crude crystals were dissolved in chloroform and the solution was subjected to silica gel column chromatography (40 g). Elution was performed with a mixture of chloroform and methanol to give N-(cholest-5-ene-3β-oxycarbonyβ-alanine (187 mg) as white powders.

Melting point : 127–130° C.
IR (chloroform); 3450, 1705 cm$^{-1}$

PREPARATION EXAMPLE 7

Tetrahydrofuran (10 ml) and cholesteryl chloroformate (449 mg) were added to a solution of 6-amino-n-caproic acid (131 mg) and sodium hydrogencarbonate (84 mg) in a mixture of tetrahydrofuran (10 ml) and water (10 ml) at 0° C. Then, following the same procedures as in Preparation Example 6, N-(cholest-5-ene-3β-oxycarbonyl)-6-amino n-caproic acid (126 mg) was obtained as white powders.

IR (chloroform): 3440, 1700 cm$^{-1}$

PREPARATION EXAMPLE 8

Cholest 5-ene-3β-oxyacetic acid (667 mg) was obtained in accordance with the method described in Aust. J. Chem., 24, 143-151 (1971).

Melting point: 160° C.

EXAMPLE 1

A solution (10.9 ml) containing 37.5 μmoles of Adriamycin in methanol and 25.9 ml of chloroform/methanol solution containing 37.5 μmoles of N-(cholest-5-ene-3β-oxycarbonyl)glycine were charged in an Erlenmeyer's flask. The organic solvent was distilled off by an evaporator. After 14.4 ml of chloroform solution containing 225.2 μmoles of yolk lecithin and 150 μmoles of cholesterol was further charged in the flask, chloroform was distilled off by the evaporator.

Next, 10 ml of 0.01 M phosphate buffered saline was added to the residue and the mixture was shaken to give the liposome suspension. The resulting liposome suspension was sequentially extruded through polycarbonate membranes (3.0, 1.0, 0.8, 0.6 and 0.4 μm). Thereafter, Adriamycin which was not entrapped in liposome was removed by dialysis in 0.001 M phosphate buffered saline at 4° C. for 48 to 72 hours. Thus, Adriamycin-entrapped liposome preparation was obtained.

EXAMPLE 2

Adriamycin-entrapped liposome preparation was obtained in a manner similar to Example 1, except for using 37.5 μmoles of N-(cholest-5-ene-3β-oxycarbonyl)glycyl-glycine in place of 37.5 μmoles of N-(cholest-5-ene-3β-oxycarbonyl)glycine of Example 1.

EXAMPLE 3

Adriamycin-entrapped liposome preparation was obtained in a manner similar to Example 1, except for using 37.5 μmoles of N-(cholest-5-ene-3β-oxycarbonyl)glycyl-glycylglycine in place of 37.5 μmoles of N-(cholest-5-ene-3β-oxycarbonyl)glycine of Example 1.

EXAMPLE 4

Adriamycin-entrapped liposome preparation was obtained in a manner similar to Example 1, except for using 37.5 μmoles of N-(cholest-5-ene-3β-oxycarbonyl)-4-amino-methylbenzoic acid in place of 37.5 μmoles of N-(cholest-5-ene-3β-oxycarbonyl)glycine of Example 1.

EXAMPLE 5

Adriamycin-entrapped liposome preparation was obtained in a manner similar to Example 1, except for using 37.5 μmoles of N-(cholest-5-ene-3β-oxycarbonyl)-4-aminophenylacetic acid in place of 37.5 μmoles of N-(cholest-5-ene-3β-oxycarbonyl)glycine of Example 1.

EXAMPLE 6

Adriamycin-entrapped liposome preparation was obtained in a manner similar to Example 1, except for using 37.5 μmoles of N-(cholest-5-ene-3β-oxycarbonyl)-β-alanine in place of 37.5 μmoles of N-(cholest-5-ene-3β-oxy-carbonyl)glycine of Example 1.

EXAMPLE 7

Adriamycin-entrapped liposome preparation was obtained in a manner similar to Example 1, except for using 37.5 μmoles of N-(cholest-5-ene-3β-oxycarbonyl)-6-amino-n-caproic acid in place of 37.5 μmoles of N-(cholest-5-ene-3β-oxycarbonyl)glycine of Example 1.

EXAMPLE 8

Adriamycin-entrapped liposome preparation was obtained in a manner similar to Example 1, except for using 37.5 μmoles of cholest-5-ene-3β-oxyacetic acid in place of 37.5 μmoles of N-(cholest-5-ene-3β-oxycarbonyl)glycine of Example 1.

While the invention has been described in detail and with reference to specific embodiments thereof, it is apparent to one skilled in the art that various changes and modifications can be made therein without departing from the spirit and the scope of the present invention.

What is claimed is:

1. A liposome preparation comprising as a liposome membrane constituent N-(cholest-5-ene-3β-oxycarbonyl)glycine, in which Adriamycin is entrapped.

2. A liposome preparation comprising as a liposome membrane constituent N-(cholest-5-ene-3β-oxycarbonyl)glycyl-glycine, in which Adriamycin is entrapped.

* * * * *